United States Patent
Klaus et al.

(10) Patent No.: US 10,569,235 B2
(45) Date of Patent: Feb. 25, 2020

(54) SIEVE-LIKE FILTER UNIT FOR CARTRIDGE-SHAPED RECEPTACLE

(71) Applicant: B. BRAUN AVITUM AG, Melsungen (DE)

(72) Inventors: Dinah Klaus, Münster (DE); Matthias Wesseler, Melle (DE)

(73) Assignee: B. Braun Avitum AG (DE)

( * ) Notice: Subject to any disclaimer, the term of this patent is extended or adjusted under 35 U.S.C. 154(b) by 289 days.

(21) Appl. No.: 15/690,883

(22) Filed: Aug. 30, 2017

(65) Prior Publication Data

US 2018/0056249 A1    Mar. 1, 2018

(30) Foreign Application Priority Data

Aug. 30, 2016   (DE) .................. 10 2016 116 097

(51) Int. Cl.
*A61M 1/16*    (2006.01)
*A61M 1/36*    (2006.01)
(Continued)

(52) U.S. Cl.
CPC ......... *B01F 1/0033* (2013.01); *A61M 1/1668* (2014.02); *A61M 1/367* (2013.01); *B01D 29/03* (2013.01); *A61M 1/1666* (2014.02); *A61M 2205/126* (2013.01); *A61M 2205/7545* (2013.01); *B01D 2201/184* (2013.01); *B01F 2001/0088* (2013.01); *B01F 2001/0094* (2013.01); *B01F 2215/0034* (2013.01)

(58) Field of Classification Search
CPC .. A61M 1/1666; A61M 1/1668; A61M 1/367; A61M 2205/126; A61M 2205/7545; B01D 29/03; B01D 35/28; B01D 2201/184; B01F 1/0033; B01F 2001/0088; B01F 2001/0094; B01F 2215/0034

See application file for complete search history.

(56) References Cited

U.S. PATENT DOCUMENTS 4,306,971 A      12/1981  Hankammer
2004/0050774 A1*  3/2004  Jerg ................... A47L 15/4208
                                                        210/498

(Continued)

FOREIGN PATENT DOCUMENTS

CA    2777850 A1   11/2013
DE    29718407 U1   1/1998
(Continued)

OTHER PUBLICATIONS

Extended European Search Report for European Application No. 17 187 369.8, dated Jan. 19, 2018, including English translation, 12 pages.

(Continued)

*Primary Examiner* — Lucas A Stelling
(74) *Attorney, Agent, or Firm* — RatnerPrestia

(57) ABSTRACT

A sieve-like filter unit, especially for a cartridge-shaped receptacle, which is arranged on a connecting port/connector of the receptacle and is designed to withhold undissolved powder and/or solid particles present in the receptacle, comprising at least two openings each being composed of at least two connected part recesses, wherein each individual opening in its entirety is formed to be extending in a non-linear manner.

13 Claims, 5 Drawing Sheets

(51) Int. Cl.
*B01D 29/03* (2006.01)
*B01F 1/00* (2006.01)

(56) References Cited

U.S. PATENT DOCUMENTS

| | | |
|---|---|---|
| 2006/0186035 A1 | 8/2006 | Tryggvason et al. |
| 2014/0124434 A1 | 5/2014 | Lee et al. |
| 2015/0029817 A1 | 1/2015 | Orszullok |

FOREIGN PATENT DOCUMENTS

| | | |
|---|---|---|
| EP | 0019794 A1 | 12/1980 |
| EP | 0532835 A2 | 3/1993 |
| EP | 1610842 A1 | 1/2006 |
| EP | 2832339 A1 | 2/2015 |
| WO | 2005118485 A1 | 12/2005 |

OTHER PUBLICATIONS

German Search Report for German Application No. 10 2016 116 097.0, dated Mar. 8, 2017 with translation, 11 Pages.

* cited by examiner

SIEVE-LIKE FILTER UNIT FOR CARTRIDGE-SHAPED RECEPTACLE

CROSS REFERENCE TO RELATED APPLICATIONS

This application claims priority to German application DE 10 2016 116 097.0 filed Aug. 30, 2016, the contents of such application being incorporated by reference herein.

FIELD OF THE INVENTION

The invention relates to a sieve-like filter unit, especially for a cartridge-shaped receptacle/a cartridge, which is arranged at a connecting port/connector of the receptacle/cartridge and is designed to withhold undissolved powder and/or solid particles present in the receptacle/cartridge and which includes at least two openings.

Moreover, the invention relates to a cartridge-shaped receptacle/a cartridge for an extracorporeal blood treatment machine including at least one connecting port/connector forming a fluid inlet and/or a fluid outlet and at least one sieve-like filter unit arranged at the at least one connecting port.

BACKGROUND OF THE INVENTION

The therapeutic success of the most diverse dialysis methods is based, inter alia, on the use of different buffer substances with the aid of which a modified acid-base metabolism of patients suffering from renal insufficiency can be corrected. Against the background that the acid-base metabolism cannot be corrected by diffusion during dialysis, frequently a supply of buffer substances is required. For balancing the gradient between acids and bases especially bicarbonate and, respectively, a bicarbonate buffer solution is suited. The bicarbonate buffer solution is produced for hemodialysis preferably immediately before or during the treatment.

The cartridge-shaped receptacles/cartridges known for this purpose basically include a fluid inlet connecting port/connector and a fluid outlet connecting port/connector to each of which a fluid inlet line and a fluid outlet line can be attached. A cartridge-shaped receptacle/a cartridge containing a bicarbonate concentrate powder thus can be connected to a fluid source, for example a water source, the water flowing through the receptacle/cartridge dissolving the bicarbonate concentrate powder present in the receptacle/cartridge and flushing the latter into the dialysis solution.

DESCRIPTION OF THE RELATED ART

It is known, inter alia, from EP 0 532 835 B1 or DE 29 718 407 U1 to provide inside the cartridge-shaped receptacle/the cartridge a sieve/filter which is adapted to withhold undissolved powder and/or solid particles such as bicarbonate, sodium chloride or the like and thus to prevent solid or powder particles from exiting the receptacle/cartridge in the undissolved state. In both documents the exact configuration of the filter is not described, however.

From EP 1 610 842 B1 a possible design of a filter/sieve disposed in a cartridge-shaped receptacle/a cartridge is known. The filter disclosed there is adapted to be mounted/attached to a bicarbonate cartridge and is configured to have slit-shaped openings. A design of filter openings in the form of slits has the drawback, however, that no sufficiently large passage area is provided while simultaneously the stability is ensured.

Especially, slits cannot be arranged/provided in any number without considerably weakening the supporting geometry and thus the stability of the filter/sieve. Due to the manufacturing process, in a filter/sieve a supporting geometry is required which is predefined especially by the design of the openings, the distance thereof from each other and the relative arrangement thereof as well as the portion of the passage area based on the total area of the filter/sieve.

Above all in the case of a small filter diameter, only an extremely limited number of slits is possible, if at the same time a satisfactory supporting geometry is still to be provided. Accordingly, especially the natural straight or linear design of slits has turned out to be detrimental. Moreover, it has turned out that slits frequently are not capable of optimally withholding the bicarbonate in the cartridge-shaped receptacle/the cartridge.

SUMMARY OF THE INVENTION

Against this background, it is an object of the invention to avoid or at least alleviate said drawbacks from the state of the art. In particular, a filter/sieve is to be provided which efficiently withholds undissolved solids or particles, at the same time improves flow of the solution through the filter/sieve and moreover ensures sufficient mechanical stability. Moreover, the filter unit is to be adapted to be easily integrated in a cartridge-shaped receptacle/a cartridge.

This object is achieved by a sieve-like filter unit as well as a cartridge-shaped receptacle/a cartridge according to the independent claims. Advantageous further developments and embodiments are claimed in the subclaims and/or shall be explained hereinafter.

First of all, the invention relates to a sieve-like filter unit, especially for a cartridge-shaped receptacle/a cartridge which is arranged on a connecting port/connector of the receptacle/cartridge and is designed for withholding undissolved powder and/or solid particles provided in the receptacle/cartridge. The sieve-like filter unit includes at least two openings each of which is composed of at least two connected partial/part recesses/opening portions/sections, wherein a non-linear/non-straight opening run is provided in a transition area/portion between at least two of the part recesses and each individual opening thus is designed in its entirety to extend in a non-linear/non-straight manner.

In other words, according to aspects of the invention, a filter/sieve for a cartridge-shaped receptacle/cartridge is provided which is intended to withhold undissolved powder and solids in the receptacle/cartridge. The filter/sieve includes at least two openings which in turn are composed of at least two part recesses/opening portions.

The openings are composed of a plurality of part recesses which may be configured both identically and non-identically. Identical part recesses are understood to be portions of the openings which have an identical or equal shape as well as identical or equal outer dimensions. Non-identical part recesses, on the other hand, are different in their shape and/or in their dimensions. For forming an opening, the part recesses may be arranged, for example, to be rotated against each other, wherein both only identical as well as only non-identical and identical as well as non-identical part recesses may form an opening, when being respectively combined. A part recess basically passes to another part recess in a transition area/portion.

Thus, the part recesses are merged in a transition area/portion and jointly form a continuous total opening or total recess. At least two of the part recesses constituting the opening have a non-linear/non-straight opening run in their transition area/portion. It has turned out that, if each individual one of the openings in its entirety is formed to be extending in a non-linear manner or to be expanding/propagating in a non-linear manner, an available passage area, especially with a small available filter diameter, especially as compared to the linear or straight slits used in prior art, can be increased to a large extent and thus the flow of the buffer solution through the sieve can be improved.

Non-linearly extending openings are thus understood to be openings or recesses according to aspects of the invention which are formed to be curved/arched or bent at least in portions between two end portions and thus run through a change in their spatial direction.

Preferably, the openings in their entirety may be configured approximately symmetrically, in particular axially symmetrically. It has turned out that exactly by a combination of features of non-linearly extending as well as approximately symmetrically designed openings a flow of the solution through the filter/sieve can be improved and, at the same time, improved stability of the supporting structure of the filter unit can be provided.

It is advantageous when the at least two connected part recesses extend away from a common point into at least two different or non-parallel directions. Accordingly, especially V-shaped, Y-shaped, X or cross-shaped or other star-shaped or radiant openings have turned out to be advantageous.

In accordance with an advantageous embodiment, the openings are star-shaped and/or radiant and include at least two, preferably three, four, five or more, beams or spikes each extending radially outwardly from a common point/transition point/intersection, especially center. The common point/transition point/intersection may also be eccentrically arranged, however.

Advantageously, each of the openings spans a circle and/or a dimension/extension of the openings in a first direction is identical to a dimension/extension of the openings in a second direction which is preferably perpendicular to the first direction.

In other words, the advantages of the present invention are definitely achieved by the compact non-elongate shape of the openings which are composed of part recesses extending away from a common point into non-parallel directions and which span a circle and/or a square. In particular, said features serve for improved fluid flow through the filter/sieve and, in connection with an axially symmetric configuration of the openings and/or a uniform distribution of the spikes/beams around a common center, also serve for improved stability. According to aspects of the invention, thus a more stable supporting structure and, at the same time, an enlarged passage area are provided.

Alternatively or additionally, the openings may be wave-shaped and/or meander-shaped and/or may be serrated, hook-shaped or point-shaped. Furthermore, according to aspects of the invention, stepped, point-shaped, rectangular, semicircular or parabolic openings are imaginable. In addition, openings in the form of interrupted circles and/or interrupted squares may be provided.

It is of advantage when the openings are arranged at the, especially circular, filter unit at least approximately evenly spread and/or are located with their centers or transition points on one out of at least two circles concentric to each other, wherein especially a number of openings located on one of the concentric circles increases from a radial inside toward a radial outside and/or a size of the openings is the larger the fewer concentric circles on which the openings are arranged are provided.

According to aspects of the invention, it is especially important to appropriately distribute the plurality of provided openings on the circular filter unit. Only by uniform distribution of the openings accompanied by an appropriate shape of the openings can a sufficient stability be reached, even when the passage area is increased. Accordingly, it has turned out that it is advantageous to arrange the recesses with their centers or transition points on one out of two, three, four or more concentric circles provided and to preferably distribute them evenly, i.e. at a uniform angular distance, along the circumference of a concentric circle. The openings are preferably arranged symmetrically on the filter unit, but they may as well be arranged asymmetrically.

In accordance with a preferred embodiment of the present invention, a plurality of star-shaped and/or radiant identical openings/recesses having four or five beams/spikes are provided on the sieve-like filter unit which are arranged with the centers/transition points thereof on two circles concentric to each other. Preferably the openings are arranged to be evenly spread.

It is useful when an arrangement and/or a number and/or a geometry of the openings is selected depending on the diameter of the filter/sieve.

The filter unit according to aspects of the invention has a very small preferred diameter. Due to the fact that, in accordance with the invention, use is not made of slits but of the afore-described openings, even with a small diameter of the filter/sieve a suitable total passage area of the openings can be provided while meeting the requirements to stability. Hence, the arrangement, the number and the geometry of the openings, respectively, are optimized according to aspects of the invention, as regards a ratio of the passage area to the total area while simultaneously meeting the requirements to stability.

Of course, meeting the requirements of stability is also always dependent on the given depth of the filter unit. According to aspects of the invention, the depth of the filter/sieve is somewhat larger than or equal to a maximum width of the part recesses of the openings.

According to aspects of the invention, it is provided for the part recesses of the openings not to exceed a predetermined maximum width that is especially predetermined by the powder and/or solid particles present in the receptacle. The part recesses of the openings in other words are thus configured to be preferably narrow and/or elongated.

In an advantageous embodiment the openings include rounded outer edges circumferentially/over the full periphery. Rounded outer edges of the openings have equally proven to be very advantageous especially with respect to meeting the requirements to stability.

Rounded outer edges offer the advantage that no notching effect will occur and the openings will not tear.

Summing up, the present invention provides a filter/sieve having a suitable number of openings of specific geometry and arrangement relative to each other. In particular, the invention makes available a filter/sieve which provides a sufficiently large passage area while ensuring stability and in addition prevents undissolved solid particles from exiting the receptacle/cartridge. In other words, according to aspects of the invention the passage area is optimized relative to the total area. The filter/sieve may basically be formed in one piece/in one material/in one part/integrally/adhesively with the receptacle or may be received by form fit in the same, especially in a connecting port of the receptacle.

Furthermore, the invention relates to a cartridge-shaped receptacle/a cartridge for an extracorporeal blood treatment machine which includes at least one connecting port/connector forming a fluid inlet and/or a fluid outlet and at least one sieve-like filter unit disposed on the at least one connecting port, especially as afore-described, the filter unit being designed to withhold undissolved powder and/or solid particles present in the receptacle/cartridge.

Preferably the filter unit is manufactured in one material and/or in one piece and/or integrally and/or in one part with the receptacle/cartridge.

According to aspects of the invention, especially the cartridge-shaped receptacle/the cartridge along with the at least one connecting port and the at least one filter unit is manufactured from plastic material in a process step during injection molding. The receptacle/cartridge may consist of a base component and a cover component each of which includes a connecting port. In this case, both the base component with the dedicated connecting port and the filter unit and the cover component with the dedicated connecting port and the filter unit are manufactured in one process step by injection molding.

In other words, the filter unit is fully automatically integrated in the connecting ports of the receptacle/cartridge in one single process step. Consequently, according to aspects of the invention, the filter/sieve need not be inserted into the connecting port(s) of the receptacle/cartridge in a second process step. This design of the filter unit in one part with the connecting ports entails a reduction of material and manufacturing costs. Moreover, the one-part and bonded integration of the filter unit in the connecting ports/connectors enhances a mechanical stability of the filter unit.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
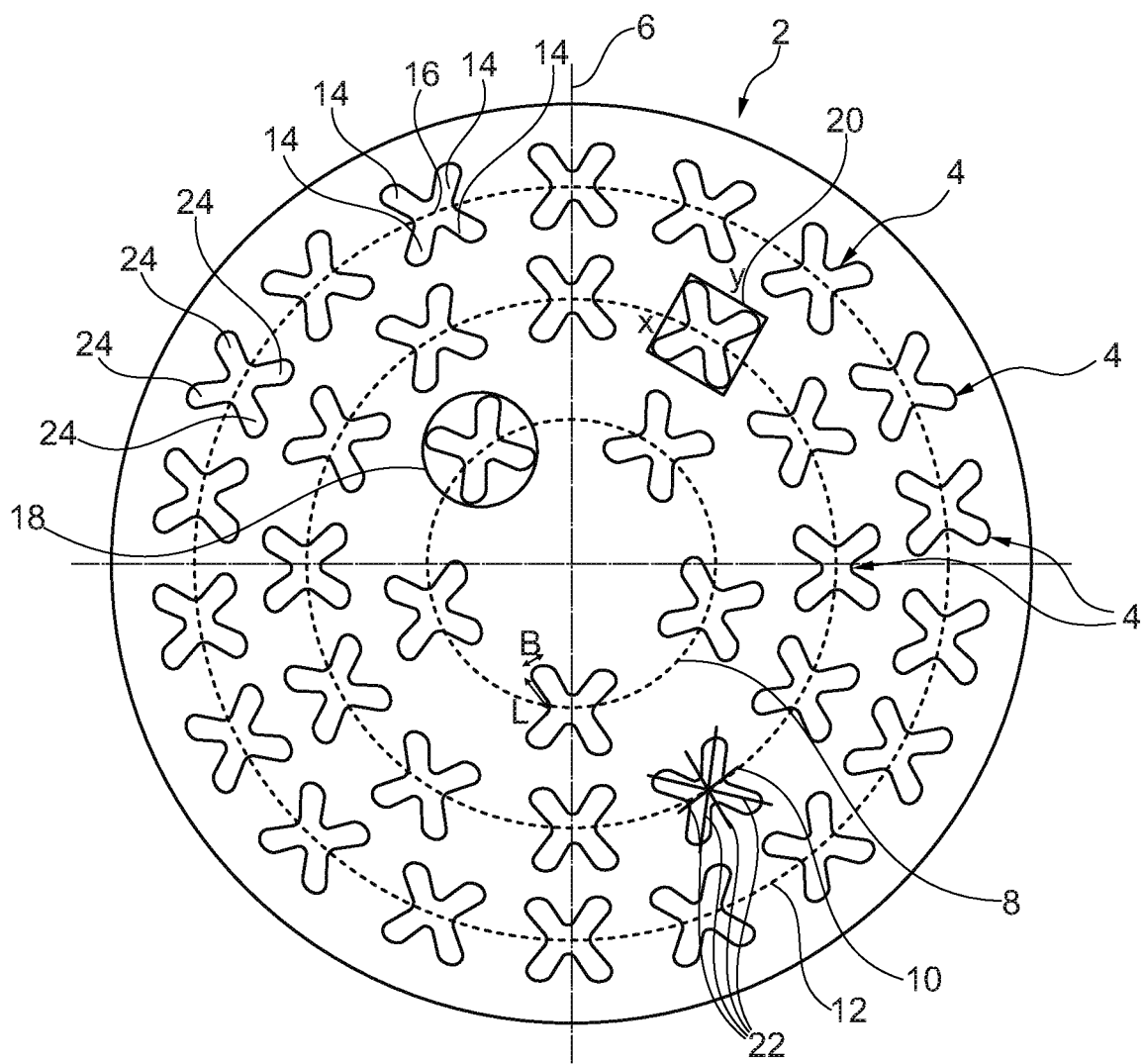
FIG. 1 shows a first preferred embodiment of a sieve-shaped filter unit according to aspects of the invention.

The Figures are merely schematic and exclusively serve for the comprehension of the invention. Like elements are provided with like reference numerals. The features of the individual embodiments may be interchanged.

In FIG. 1 a first preferred embodiment of a sieve-like filter unit 2 is illustrated. The filter unit 2 includes 35 openings 4 which at first sight are provided to be approximately evenly spread on the filter unit 2 as well as to be axially symmetric to a symmetry axis 6 of the filter. Five of the openings 4 are located on an inner circle 8, twelve of the openings 4 are located on a central circle 10 and eighteen of the openings 4 are located on an outer circle 12. This also means that there is no opening 4 provided in a center of the filter unit. At the individual circles 8, 10, 12 the provided openings 4 are spaced evenly, i.e. at equal angular distance relative to each other. The circles 8, 10, 12 are concentric to each other.

All of the openings 4 of FIG. 1 are identical and each of them takes a radiant shape/star shape. Each of the openings 4 consists of four connected, preferably identical, part recesses 14 which converge into a common center 16 and, respectively, extend away therefrom into different directions. In an area around the common center 16 transition areas/portions 17 are provided between the part recesses 14. At least the directly adjacent, i.e. not facing, part recesses 14 are extending in their transition area/portion 17 in a non-linear or non-straight manner. As is evident from FIG. 1, the openings span an opening circle 18 or an opening square 20. The opening square 20 illustrates that an extension x of the openings 4 is identical to or of equal length with an extension y perpendicular thereto of the openings 4. Each of the openings 4 of FIG. 1 includes four symmetry axes 22 of the opening. By the part recesses 14 of FIG. 1 four beams/spikes 24 are defined for each opening 4. Each part recess 14 has a width B and a length L. The length L is longer than the width B. The width B is not allowed to exceed a predetermined maximum width $B_{max}$ so that powder and, respectively, solid particles cannot pass through the openings 4. The openings 4 are rounded at each of their outer edges.

Figure 2:
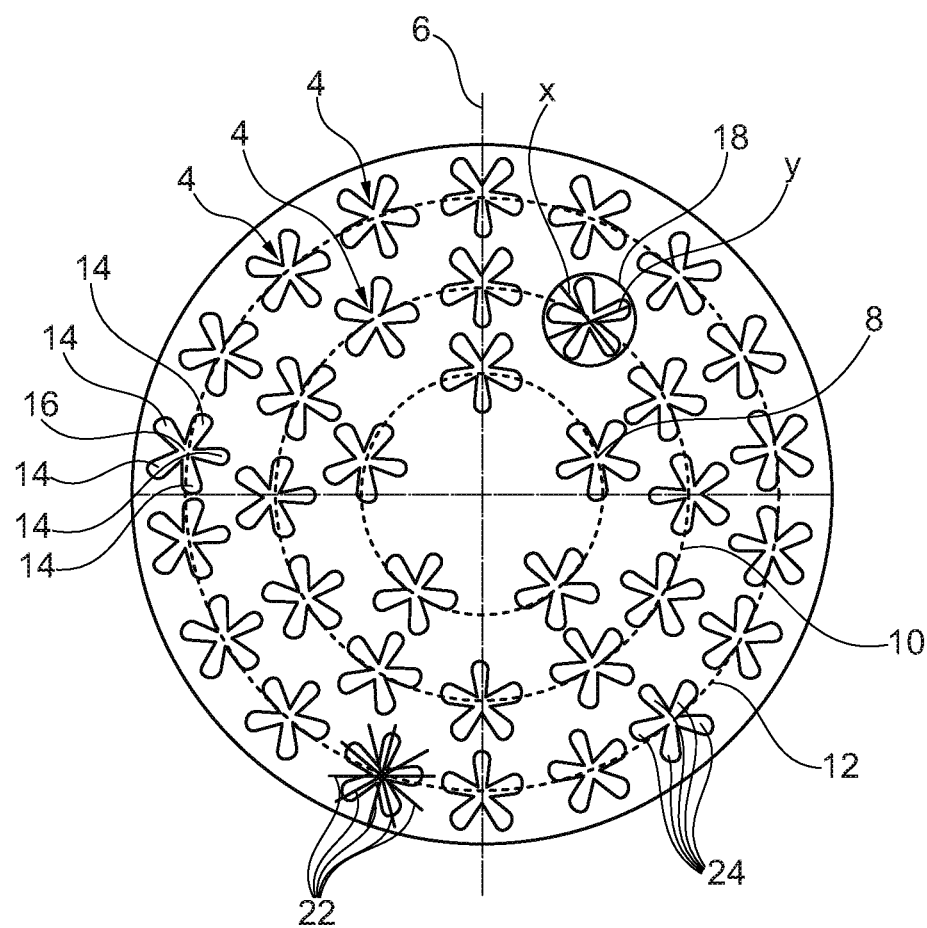
FIG. 2 shows a second preferred embodiment of the sieve-shaped filter unit according to aspects of the invention.

FIG. 2 illustrates a second preferred embodiment of the sieve-like filter unit 2. The filter unit 2 again has 35 openings 4. The arrangement of the openings 4 relative to each other is identical to the arrangement presented in FIG. 1, which is why a description will not be repeated. Hereinafter merely the differences between FIG. 1 and FIG. 2 shall be discussed.

All of the openings 4 of FIG. 2 are equally identically formed and also take a respective radiant shape/star shape. Each of the openings 4 of FIG. 2 includes five connected identical part recesses 14, however, which converge to a common center 16 and, respectively, extend away therefrom into different directions. Again, transition areas/portions 17 are provided between the part recesses 14, in an area around the common center 16. In this case, in the transition area/portion 17 between two optional ones of the five part recesses 14 a non-linear or non-straight run of the opening is provided. As is evident from FIG. 2, the openings 4 of FIG. 2 span an opening circle 18. Thus, it is also applicable to the openings 4 of FIG. 2 that an extension x of the openings 4 has a length equal to that of an extension y perpendicular thereto of the openings 4. Each of the openings 4 of FIG. 2 has five symmetry axes 22 of the opening. The part recesses 14 of FIG. 2 define five beams/spikes 24 for each opening 4. Otherwise, the description of FIG. 1 is applicable mutatis mutandis to FIG. 2.

Figure 3:
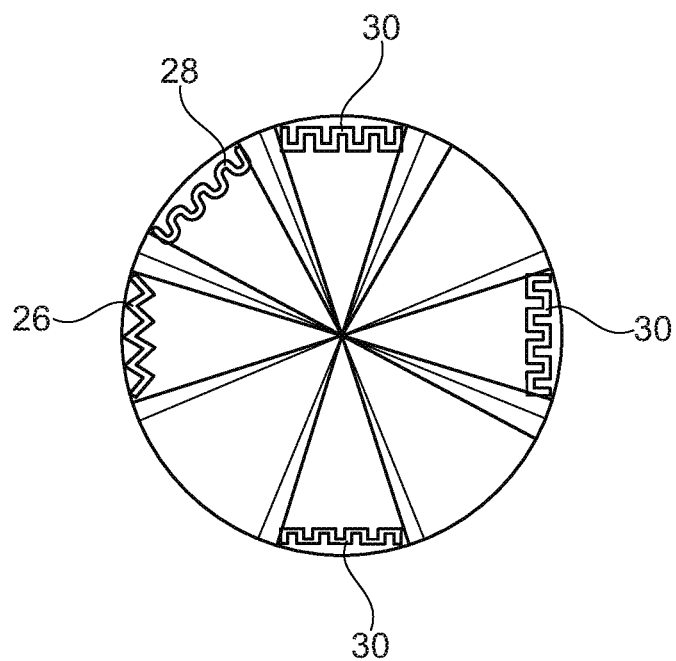
FIG. 3 shows a filter unit having further openings according to aspects of the invention.
Figure 4:
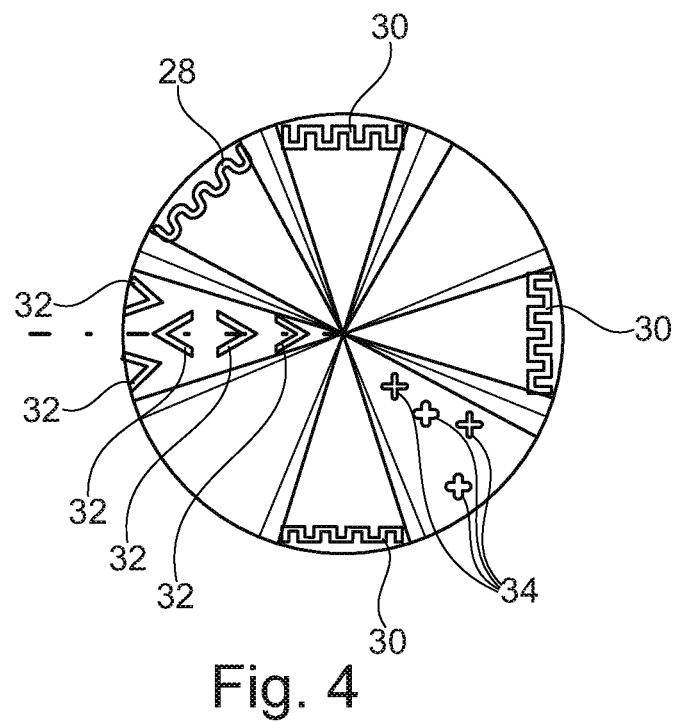
FIG. 4 shows a filter unit equally having further openings according to aspects of the invention.

FIGS. 3 and 4 merely illustrate different further openings which are imaginable in accordance with the present invention. In FIG. 3 one serrated opening 26, one wave-shaped opening 28, three meander-shaped openings 30 are shown. In FIG. 4 one wave-shaped opening 28, three meander-shaped openings 30, five hook-shaped openings 32 and four cross-shaped openings 34 are shown. The cross-shaped openings 34 may or may not have rounded edges. All of the openings shown in FIG. 3 and FIG. 4 may be provided to be evenly spread on the filter unit 2 according to aspects of the invention instead of the star-shaped/radiant openings of FIG. 1 and FIG. 2. Also, different openings according to aspects of the invention may be provided on a filter unit 2. In other words, not all of the openings need to be identical, as this is the case in FIGS. 1 and 2.

Figure 5:
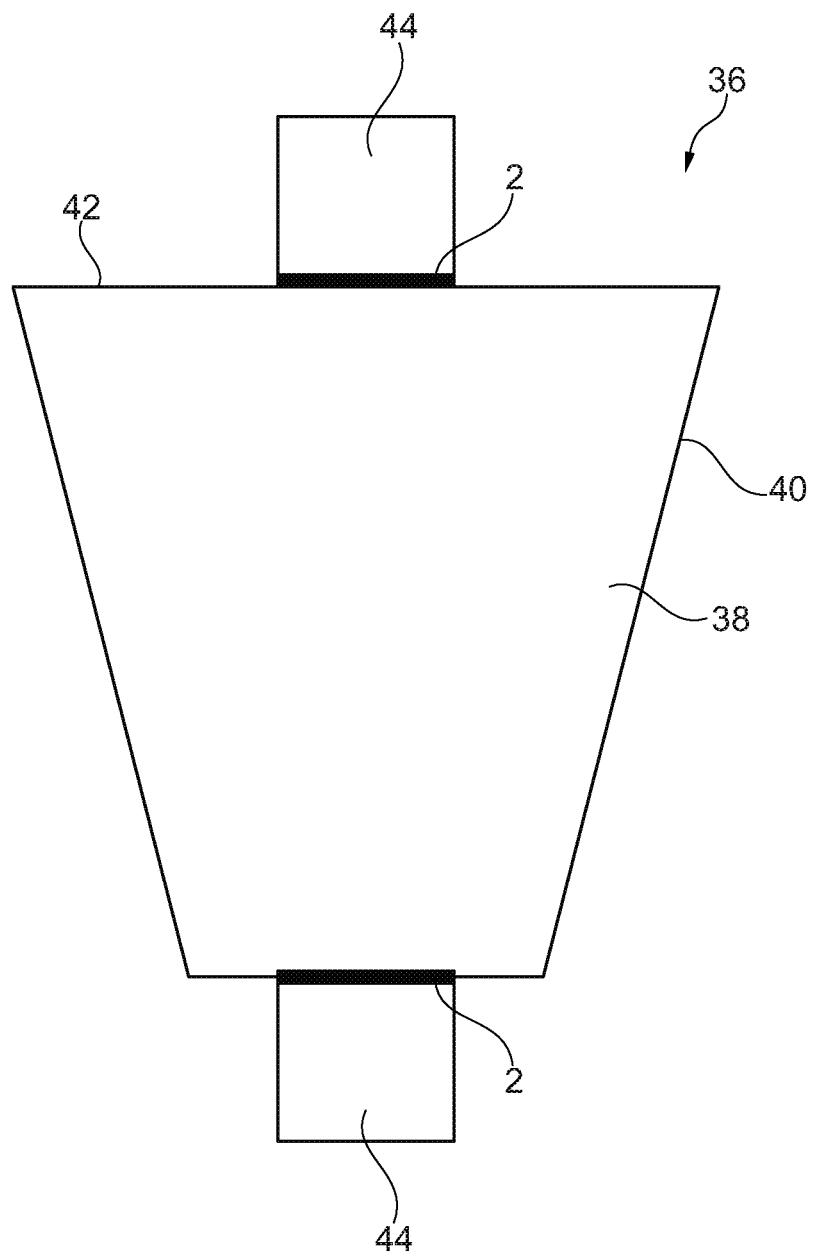
FIG. 5 shows a cartridge-type receptacle/a cartridge including two filter units according to aspects of the invention.

In FIG. 5 a cartridge 36 is illustrated which is preferably composed of a base component 40 and a cover component 42. The cartridge 36 has pipe socket-type connecting ports/connectors 44 forming a fluid inlet and a fluid outlet at two opposite axial ends. At each of the two connecting ports 44 filter units 2 are provided. The filter units 2 include the openings 4 shown in FIGS. 1 to 4 and enable fluid to flow and undissolved particles to be withheld. The cover component 42, the dedicated, upper connecting port 44 in FIG. 5 as well as the dedicated, upper filter unit 2 in FIG. 5 are manufactured as a one-piece component in one process step by injection molding. The base component 40, the dedicated, lower connecting port in FIG. 5 as well as the dedicated, lower filter unit 2 in FIG. 5 are equally manufactured as a one-piece component in one process step by injection molding.

Figure 6:
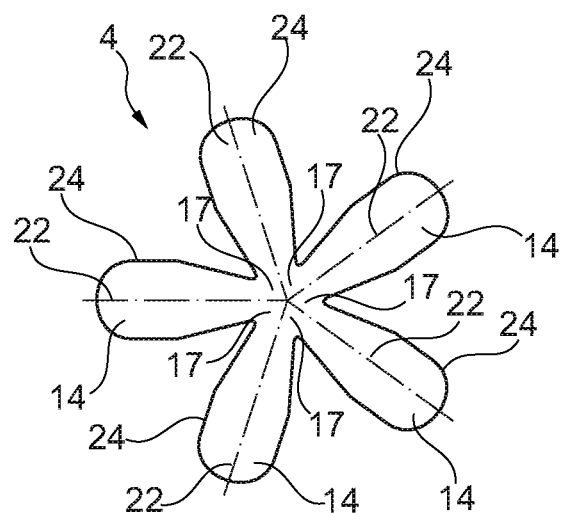
FIG. 6 shows an axially symmetric opening according to aspects of the invention consisting of five part recesses.

FIG. 6 illustrates a radiant or star-shaped opening 4 according to aspects of the invention which consists of five part recesses 14 and, respectively, five beams/spikes 24. The opening 4 of FIG. 6 is axially symmetric and has five symmetry axes 22 of the opening. A non-linear run of the opening is provided between two optional ones of the five part recesses 14 in a transition area 17. An outer contour of the opening 4 is rounded.

Figure 7:
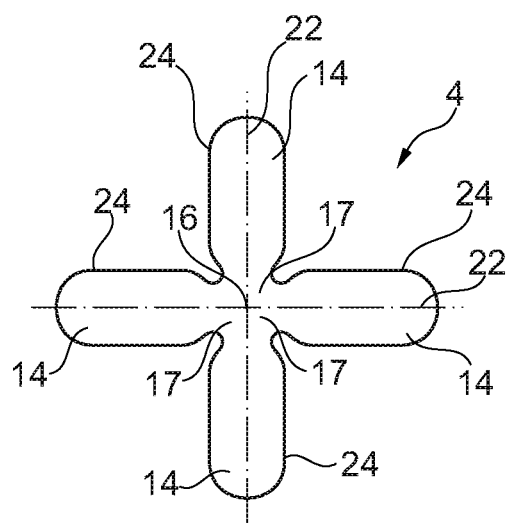
FIG. 7 shows a point-symmetric opening according to aspects of the invention consisting of four part recesses.

FIG. 7 illustrates another radiant or star-shaped opening 4 according to aspects of the invention which consists of four part recesses 14 and, respectively, four beams/spikes 24. The opening 4 of FIG. 7 is formed to be axially symmetric having two axes of symmetry 22 and to be point-symmetric with respect to the center 16. Between two adjacent part recesses 14 perpendicular to each other a non-linear run of the opening is given in a transition area 17. An outer contour of the opening 4 is equally rounded. Furthermore, rounded transitions withdrawn at the outer contour are provided between two part recesses 14.

Figure 8:
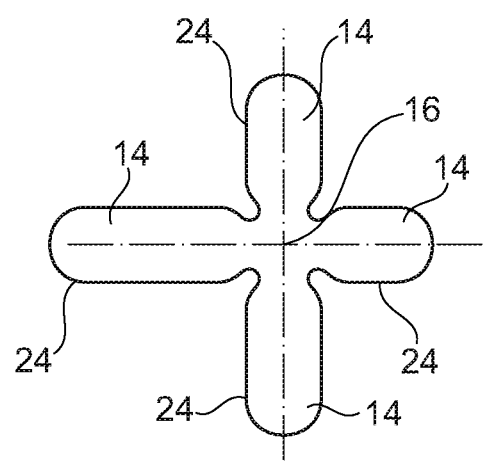
FIG. 8 shows an asymmetric opening according to aspects of the invention consisting of four non-identical or different part recesses.

FIG. 8 illustrates another radiant or star-shaped opening 4 according to aspects of the invention which consists of four part recesses 14 and, respectively, four beams/spikes 24. The opening 4 of FIG. 8 is asymmetric. All of the four part recesses 14 have different sizes and different outer dimensions, respectively. Thus, the part recesses 14 are not identical, but they extend, as this is also the case in the embodiments of FIG. 6 and FIG. 7, away from a common intersection/transition point 16, which in this case is no center, into two non-parallel directions. An outer contour of the opening 4 is equally rounded. Furthermore, at the outer contour also withdrawn rounded transitions are provided between two part recesses 14.

A plurality of identical openings 4 but also a plurality of different openings 4 may be provided at the filter unit 2 of the present invention.

The invention claimed is:

1. A filter unit for a cartridge-shaped receptacle to be arranged on a connecting port of the cartridge-shaped receptacle, the filter unit configured to withhold at least one of undissolved powder or solid particles present in the cartridge-shaped receptacle, the filter unit defining a filter center point and comprising:
   a plurality of openings, each opening comprising at least two connected part recesses extending from a common center point of said opening, each opening also comprising a non-linear run provided in a transition area between of the at least two part recesses such that each opening extends in a non-linear manner with the at least two part recesses being symmetrical to one another about a symmetry axis,
   the plurality of openings being arranged with their respective common center points located on at least one circle extending around the filter center point,
   each opening having its symmetry axis passing through its common center point and through the filter center point,
   the symmetry axis of a first opening of the plurality of openings extending at an acute angle relative to the symmetry axis of a second opening of the plurality of openings, so that the first opening and the second opening have different orientations relative to the filter center point.

2. The sieve like filter unit according to claim 1, wherein the at least two connected part recesses extend away from a common point in at least two non-parallel directions.

3. The filter unit according to claim 1, wherein each of the openings spans the at least one circle.

4. The filter unit according to claim 1, wherein each of the openings are at least one of star-shaped or radiant and have at least two beams and/or spikes each extending radially outwardly from a common point.

5. The filter unit according to claim 4, wherein the common point is at least one of the common center point of said opening, a transition point, or an intersection point between the at least two connected part recesses.

6. The filter unit according to claim 1, wherein each of the at least two openings are wave-shaped, meander-shaped, serrated and/or hook-shaped, or point-shaped.

7. The filter unit according to claim 1, wherein the openings are evenly spread on the filter unit.

8. The filter unit according to claim 1, wherein each of the openings have rounded outer edges over their entire circumference.

9. The filter unit according to claim 1, wherein for each opening, an extension of said opening in a first direction is identical to an extension of said opening in a second direction.

10. The filter unit according to claim 1, wherein the at least one circle comprises a first circle and a second circle, the first circle and the second circle being concentric, the openings comprising a first number of openings arranged on the first circle and a second number of openings arranged on the second circle, the second number of openings being greater than the first number of openings.

11. The filter unit according to claim 1, wherein the at least two connected part recesses comprise four connected part recesses.

12. A cartridge-shaped receptacle for an extracorporeal blood treatment machine, the cartridge-shaped receptacle comprising:
   at least one connecting port forming at least one of a fluid inlet or a fluid outlet;
   at least one filter unit according to claim 1, each of the at least one filter unit disposed on a corresponding one of the at least one connecting port.

13. The cartridge-shaped receptacle according to claim 12, wherein the each of the at least one filter unit is manufactured at least one of from one material, in one piece, integrally with the cartridge-shaped receptacle, or in one part with the cartridge-shaped receptacle.

* * * * *